United States Patent [19]

Shapiro

[11] Patent Number: 5,571,071
[45] Date of Patent: Nov. 5, 1996

[54] LARYNGOSCOPE BLADE INCLUDING MEANS FOR DISPENSING TOPICAL ANESTHETIC

[76] Inventor: Jeffrey M. Shapiro, 21 Quail La., San Carlos, Calif. 94070

[21] Appl. No.: 512,295

[22] Filed: Aug. 8, 1995

[51] Int. Cl.$^6$ ................................................. A61B 1/267
[52] U.S. Cl. ........................... 600/187; 600/185; 600/190
[58] Field of Search .................................... 600/185, 187, 600/188, 190, 192

[56] References Cited

U.S. PATENT DOCUMENTS

| 2,854,004 | 2/1957 | Durrant | 600/187 X |
| 4,384,570 | 5/1983 | Roberts | 600/187 |
| 4,947,896 | 8/1990 | Bartlett | 600/187 |

*Primary Examiner*—Richard J. Apley
*Assistant Examiner*—David R. Risley
*Attorney, Agent, or Firm*—Paul D. Grossman

[57] ABSTRACT

An improved laryngoscope blade is described wherein the blade includes an anesthetic-containing reservoir. In a first preferred embodiment for providing an anesthetic spray at the distal end of the blade, the blade includes a conduit for providing fluid communication between the reservoir and the distal end of the blade and a fluid delivery means for expelling the anesthetic from the reservoir and for propelling it through the conduit. In a second preferred embodiment for providing an anesthetic gel to the upper surface of the blade, the blade includes a fluid conduit manifold for providing fluid communication between the reservoir and the upper surface of the blade. In an alternative preferred embodiment for providing an anesthetic gel to the tipper surface of the blade, the blade includes a porous layer located on the upper surface of the blade, the porous layer being adapted to contain an anesthetic gel.

4 Claims, 6 Drawing Sheets

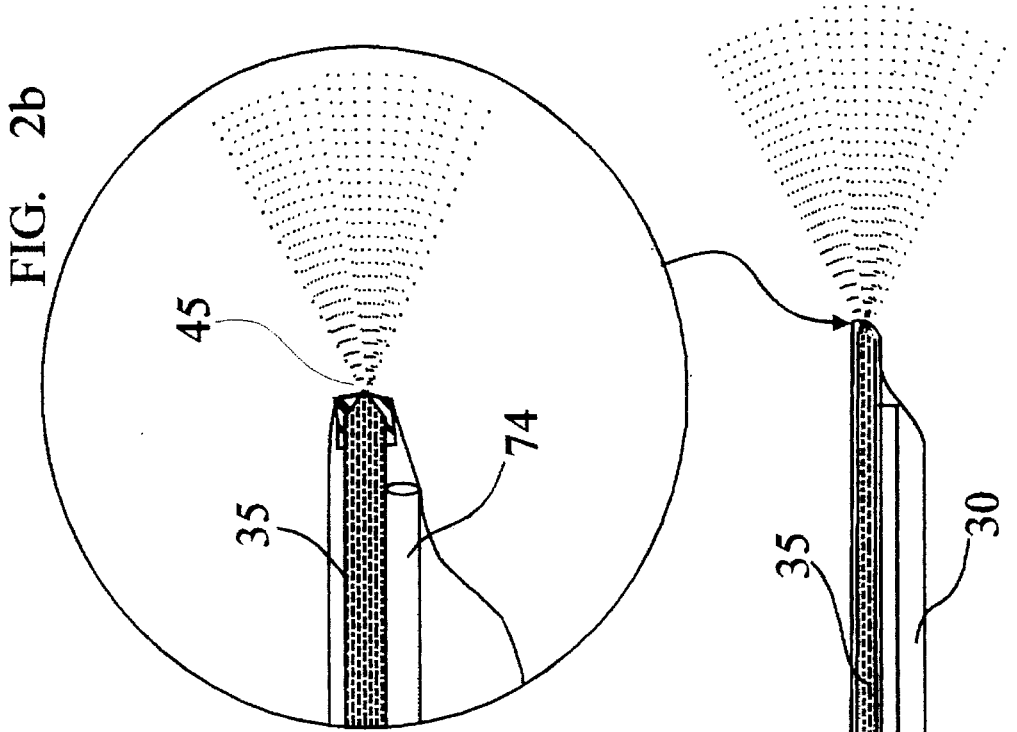
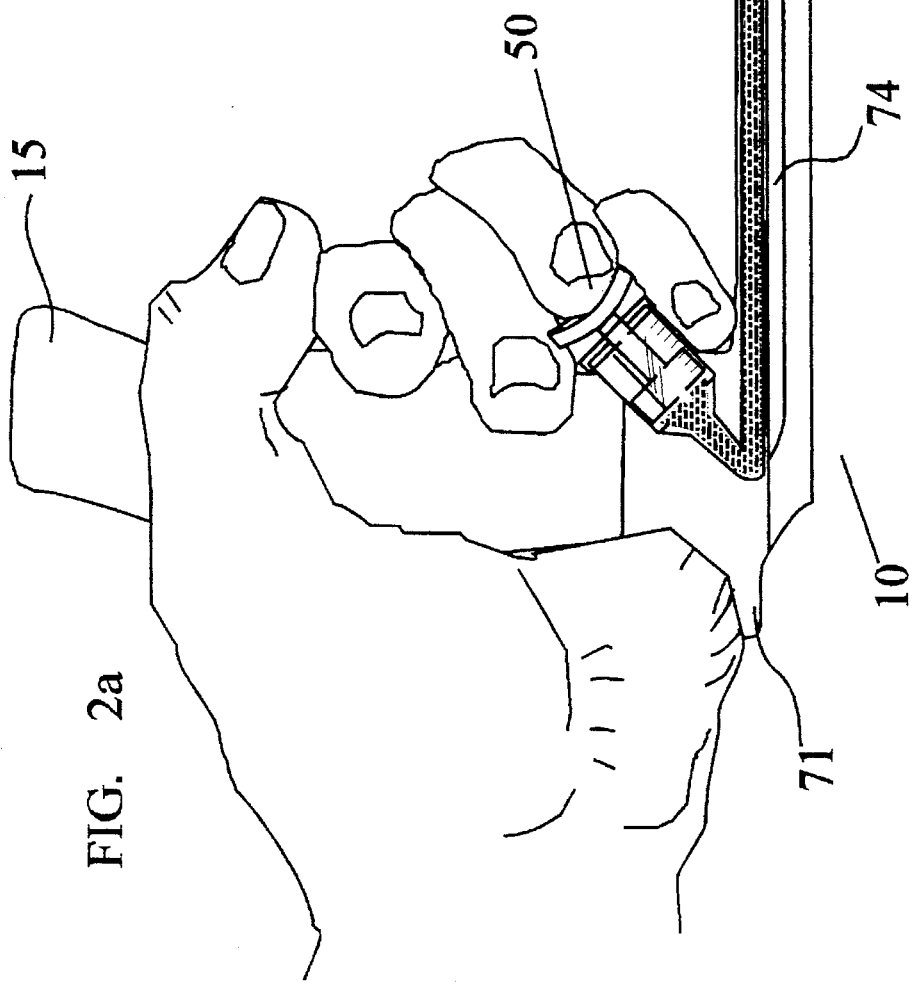

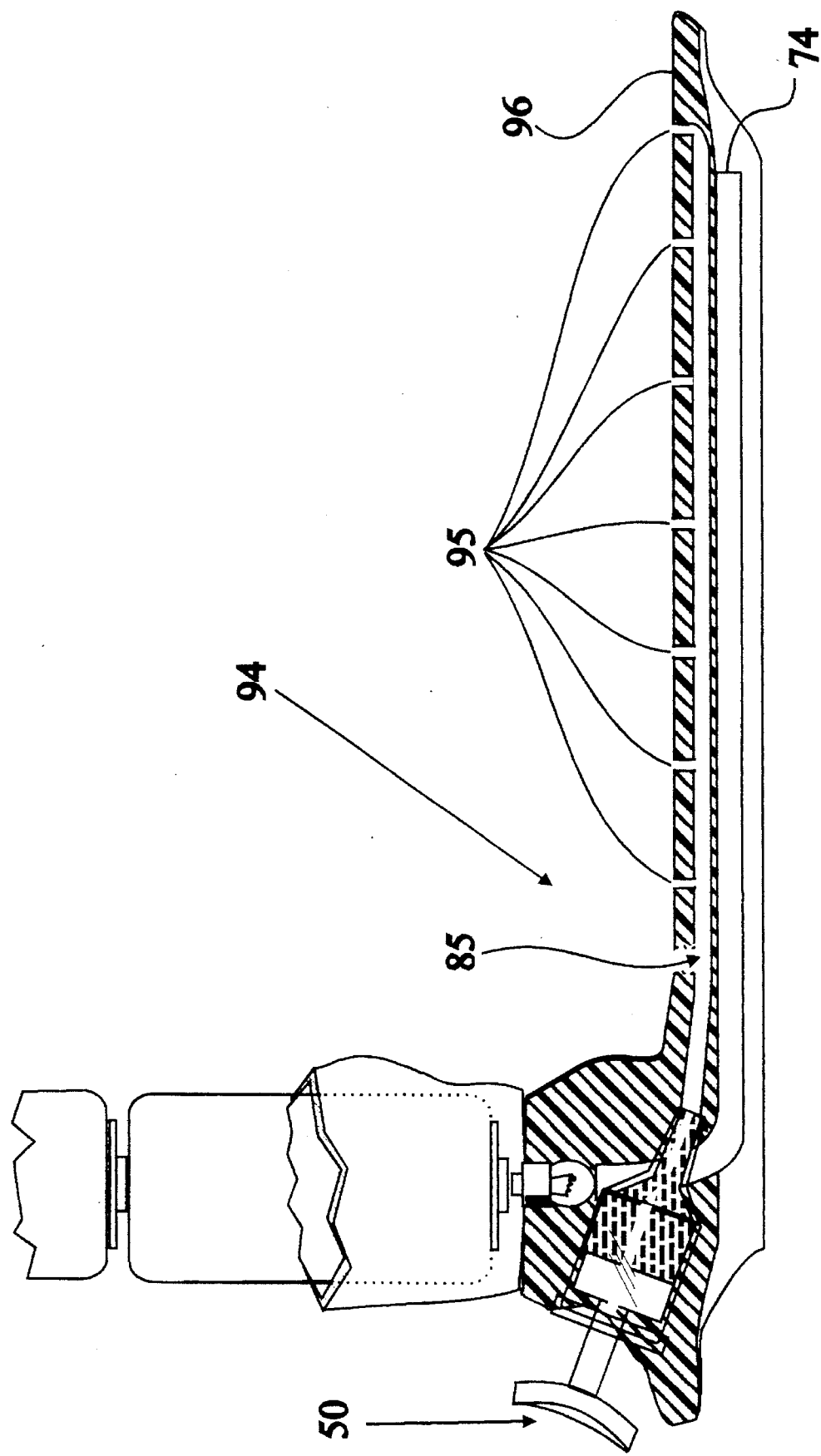

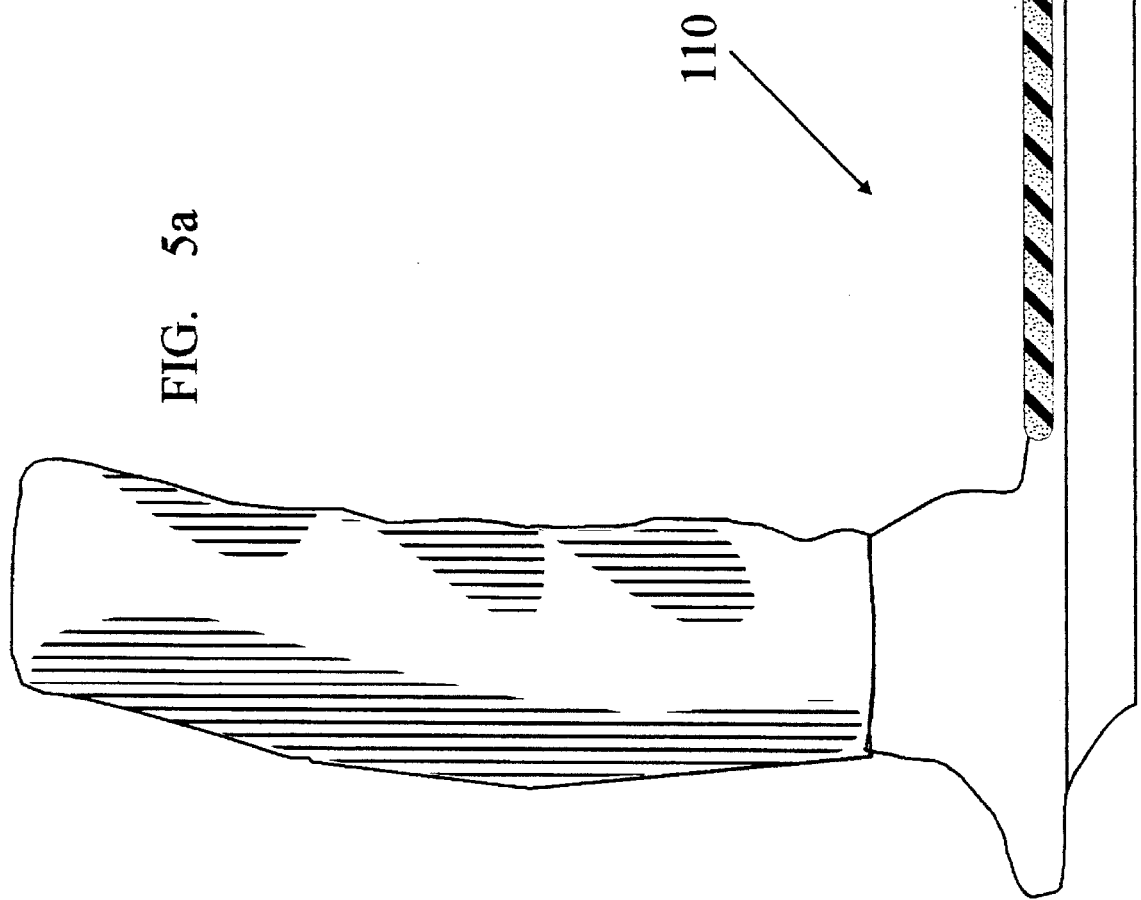

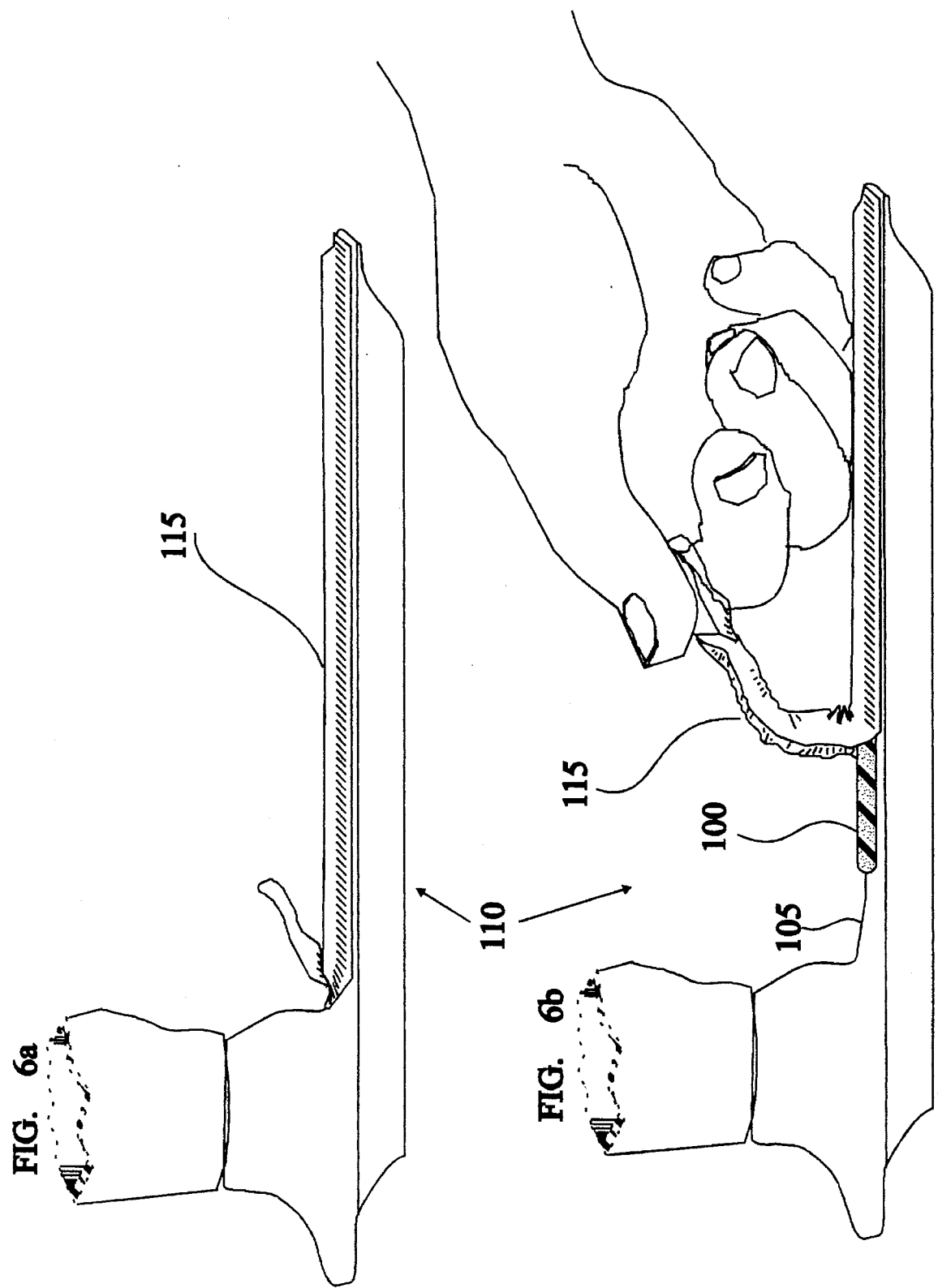

LARYNGOSCOPE BLADE INCLUDING MEANS FOR DISPENSING TOPICAL ANESTHETIC

FIELD OF THE INVENTION

The present invention relates to apparatus useful for facilitating the insertion of an endotracheal tube into a patient. More particularly, the present invention is directed to an improved laryngoscope blade including means for administering a topical anesthetic.

BACKGROUND

Often during the delivery of medical care it is necessary to ensure adequate ventilation of the ill or anesthetized patient who is unable to sustain adequate respiration. The term airway management refers to the methods by which ventilation is provided to such patients, e.g., Stone, D. J. and Gal, T. J., in Anesthesia $4^{th}$ Edition, Miller, R. D., ed., Chapter 42, Churchill-Livingston, Inc., New York (1994).

A common form of airway management involves the insertion of a tube into the pharynx and larynx of a patient for the purpose of establishing an unobstructed airway into the lungs, a process called intubation. Laryngoscopy, a first step in the intubation process, allows visualization of the pharynx and larynx during the intubation procedure. A laryngoscope is an instrument which facilitates the laryngoscopy procedure.

Typically, the laryngoscope includes a blade and a handle. The blade is inserted into the pharynx of the patient through the mouth and the handle is held by the operator and used to control the position of the blade. The blade may be detachably mounted to the handle, e.g., U.S. Pat. No. 2,630,114.

Laryngoscopy and intubation are powerful noxious stimuli, each individually being capable of eliciting a severe adverse cardiovascular response. In fact, deeper levels of anesthesia are required to blunt the body's response to laryngoscopy and intubation than are required to blunt the response to a surgical incision, e.g., Yakaitis et al., Anesthesiology, 47:386(1977), and Yakaitis et al., Anesthesiology, 50:59(1979). Deepening the level of anesthesia, giving intravenous cardiovascular drugs, performing local anesthesia nerve blocks, and applying topical anesthetics directly to the oral airway, pharynx, and larynx are all common techniques for lessening the adverse consequences of laryngoscopy and intubation. Topical administration of local anesthetics has the most specific action and the least side effects.

Typically, nothing is done to ablate the response to the insertion of the laryngoscope blade into the oral airway of the patient. Only in extreme cases is an anesthetic spray administered into the mouth prior to blade insertion.

To ablate the response to the insertion of the endotracheal tube, the pharynx and larynx are sprayed with a topical anesthetic spray. Currently, the administration of the anesthetic spray during laryngoscopy requires the use of a two-step, two-handed procedure: the laryngoscope blade is first inserted into the mouth of the patient, then, once a view of the larynx is established, holding the laryngoscope with one hand, the operator sprays the pharynx, larynx, and trachea with a topical anesthetic, using his other hand to hold the anesthetic container and dispense the anesthetic. This second step usually requires the operator to look away from the larynx to pick up the local anesthetic dispenser. While looking away, it is not uncommon for the operator to lose his view of the pharynx and larynx, requiring him to reestablish such view, thereby complicating the intubation procedure. Because this procedure is performed while the patient is not breathing, it is important that it be performed as quickly as possible.

One solution to the problem of simplifying the administration of the topical anesthetic spray while operating a laryngoscope is disclosed by Breslau in U.S. Pat. No. 4,432,350 (Breslau). Breslau describes a laryngoscope having a reservoir for containing a topical anesthetic mounted to the handle and a conduit for delivering the anesthetic to the tip of the blade. The anesthetic is expelled from the reservoir by compressing the outer walls of the reservoir directly or with a delivery means mounted to the handle.

While the Breslau laryngoscope apparently provides a system whereby laryngoscope operation and anesthetic administration may be performed with one hand, several significant problems exist with Breslau's apparatus which have contributed to its lack of acceptance by the medical community.

In many situations it is necessary to apply a large force to the blade of the laryngoscope in order to afford an adequate view of the patient's pharynx. In these situations, the operator must grip the handle of the laryngoscope firmly with a large compressive force. While the force is being applied, the hand must remain motionless or the view of the larynx can be lost. Thus, if an anesthetic reservoir and/or delivery means is attached to the handle, it will interfere with the operator's ability to firmly grip the laryngoscope, and therefore lead to loss of proper positioning of the laryngoscope blade. Moreover, when applying a large compressive force to the handle, it is possible to inadvertently expel the anesthetic, thereby greatly complicating the procedure and even possibly harming the patient.

Another drawback of the Breslau laryngoscope is that several assembly steps are required prior to use. When a disposable blade is used, the blade must first be attached to the handle, then the reservoir must be attached to the handle, and finally the delivery conduit must be threaded along the blade such that the outlet of the conduit is precisely aligned with the distal end of the blade. Clearly this sort of multi-step assembly is not practical under time-critical circumstances.

SUMMARY

The present invention is directed to my discovery of an improved laryngoscope blade including a reservoir for containing an anesthetic and a delivery means for delivering the anesthetic. The anesthetic may be in the form of a liquid which is dispensed as a spray at the distal end of the blade, or, in the form of a gel which is used to coat the top surface of the blade.

An object of my invention is to provide a laryngoscope blade which includes a means for applying a topical anesthetic capable of operation by an operator with one hand such that the administration of the topical anesthetic does not require the operator to alter his grip on the handle or to divert his eyes from the patient.

Another object of my invention is to provide a laryngoscope blade wherein all the disposable elements are provided in a single preassembled unit.

A further object of my invention is to provide a laryngoscope wherein the handle is unobstructed.

Yet another object of my invention is to provide a laryngoscope blade in which a topical anesthetic gel can be dispensed onto the top surface of the blade.

In one embodiment, the foregoing and other objects of my invention are achieved by a laryngoscope having a blade which includes a reservoir for containing a topical anesthetic liquid and a fluid delivery means for expelling the topical anesthetic from the reservoir. Preferably, a syringe is used as a combined reservoir and fluid delivery means. A conduit is included for providing fluid communication between the reservoir and the distal end of the blade member such that when anesthetic is expelled from the reservoir, anesthetic is sprayed from the distal end of the blade onto the larynx and pharynx of a patient.

In a second embodiment, the present invention includes a blade having a fluid conduit manifold for providing fluid communication between the reservoir and an upper surface of the blade such that when an anesthetic gel is expelled from the reservoir, it coats the upper surface of the blade with such gel.

In a third embodiment, the present invention includes a blade having a porous layer located on the top surface of the blade, the porous layer being adapted to contain an anesthetic gel.

BRIEF DESCRIPTION OF THE DRAWINGS

FIGS. 2a and 2b show the embodiment of FIG. 1 in operation.

FIG. 3 shows a cutaway cross-sectional view of a second preferred embodiment of the present invention including a syringe for containing and delivering an anesthetic gel and a fluid conduit manifold for delivering the anesthetic gel to the upper surface of a blade.

FIGS. 5a and 5b show a cutaway cross-sectional view of a third preferred embodiment of the present invention including a porous layer disposed on the top surface of a blade for containing and delivering an anesthetic gel to the upper surface of the blade.

FIGS. 6a and 6b show the embodiment of FIGS. 5a and 5b in operation including a sheath for covering the porous layer.

DETAILED DESCRIPTION OF THE PREFERRED EMBODIMENT

Reference will now be made in detail to several preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents which may be included within the scope of the invention as defined by the appended claims.

The present invention is designed to provide means for administering a topical anesthetic during a laryngoscopy procedure. According to the invention, topical anesthetic may be delivered in one of two ways: (i) as a spray onto the larynx and pharynx, or (ii) as a coating for the laryngoscope blade.

Figure 1:
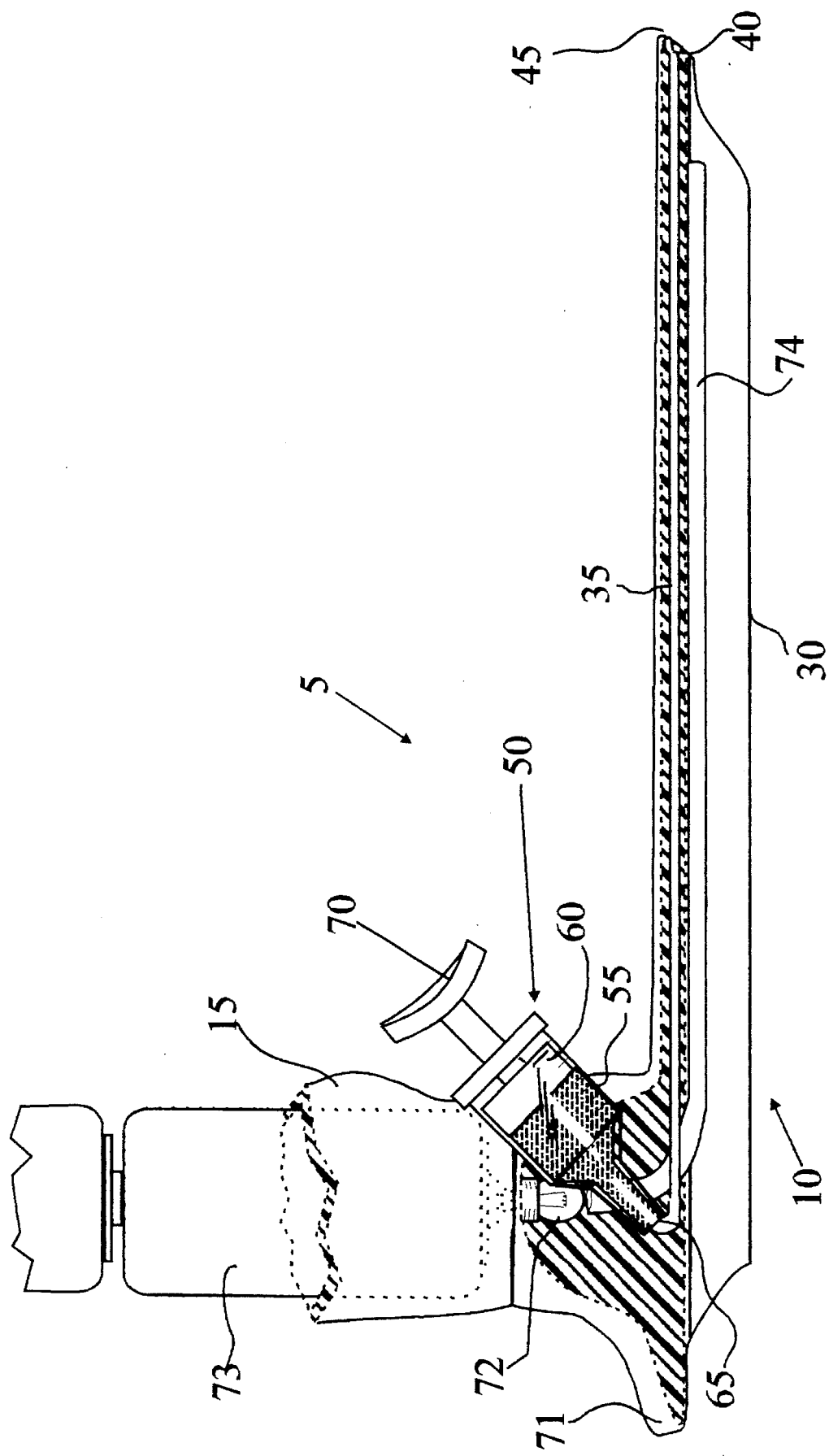
FIG. 1 shows a cutaway cross-sectional view of a preferred embodiment of the present invention including a syringe for containing and delivering an anesthetic liquid and a fluid conduit for delivering topical the anesthetic to the distal end of the blade.

Referring now to FIGS. 1, 2a and 2b a first embodiment of the present invention is directed to an improved laryngoscope (5) having a handle (15) and a blade (10) wherein the blade includes (i) a blade member (30), (ii) a reservoir for containing a topical anesthetic, (iii) a fluid delivery means for expelling the anesthetic from the reservoir, and (iv) a fluid conduit (35) for providing fluid communication between the reservoir and the distal end of the blade member (40). Note that in the embodiments shown in the figures, the reservoir and fluid delivery means are combined in a syringe (50).

Elements of the blade are mounted on the blade member (30). The blade member is of conventional shape, being either straight, i.e., a Miller blade or Wisconsin blade, or curved, i.e., a Macintosh blade. Many other types of blade members have been designed and are described elsewhere, e.g., Dorsh et al., Understanding Anesthesia Equipment, Williams and Wilkins, Baltimore (1984). Preferably, the blade member (30) is detachably mounted to one end of the handle (15).

In one important aspect of the present invention, the blade member is formed with a support flange (71) located at the proximate end of the blade member. The support flange (71) series to provide the operator a more secure hold on the laryngoscope during laryngoscopy to reduce movement of the blade during discharge of the anesthetic.

The blade member (30) is preferably made from a rigid low-cost disposable material, e.g., a rigid plastic. Particularly preferred materials include polyethylene terethlate, polysulfone, or any other suitable polymer. By making the blade member disposable, problems associated with sterilization can be eliminated by providing the blade to the user in a sealed sterilized package and directing the user to dispose of the blade after a single use. Disposability is particularly important when the laryngoscope is used in remote locations without means for sterilization available.

A reservoir is provided to contain the topical anesthetic and a fluid delivery means is provided to propel the anesthetic from the reservoir through the fluid conduit (35) to the outlet of the conduit located at the distal end of the blade member (40). The reservoir is preferably adapted to contain a predetermined measured amount of a topical anesthetic, e.g., xylocaine, cocaine, or other like topical anesthetics. Typical fluid volumes to be contained range from 2 to 4 ml.

In the preferred embodiment shown in FIG. 1, the fluid delivery means and reservoir are combined into a syringe (50) having a cylinder (55), a plunger (60), a plunger actuator (70), and a cylinder outlet (65), said cylinder outlet being in fluid communication with the inlet end of the fluid conduit (35). Preferably the cylinder (55) is graduated to indicate the fluid volume contained in the syringe. The syringe (50) is located such that the plunger actuator (70) is within easy reach of the forth and/or fifth finger of the operator during the blade-insertion procedure, where herein the fingers of the hand are numbered such that the thumb is the first finger and the pinkie finger is the fifth finger. See FIGS. 2a and 2b.

One important advantage realized by using a syringe as a combined reservoir/fluid-delivery means is that the operator can ensure complete ejection of the contents of the cylinder, i.e., there is little or no dead volume in the cylinder (55). A second important advantage of the syringe-based system is that the operator can quantitatively deliver a partial dosage of anesthetic if desired.

Preferably, the syringe (50) is mounted to the blade member (30) so as not to obstruct the operator's view of the larynx. The syringe (50) is mounted to the blade member (30) using any suitable permanent or detachable mounting means, or may be integrally formed with the blade member.

The fluid conduit (35) provides fluid communication between the syringe (50) and the distal end of the blade member (40). The inlet end of the conduit is placed in fluid communication with the cylinder (55) while the outlet end of the conduit is positioned at the distal end of the blade member (40) such that in operation, fluid leaving the conduit has an unobstructed path into the larynx. See FIGS. 2a and 2b. The internal diameter of the conduit is chosen such that it is small enough to have a small dead volume, but large enough so that the pressure drop across the conduit is not excessive, i.e., greater than a few psi. Preferred internal diameters are between 0.5 and 2 mm. Preferably, the fluid conduit (35) is secured to the blade member (30) or formed integrally therewith, as shown in FIG. 1.

In the preferred embodiment shown in FIG. 1, a dispensing nozzle (45) is attached to the outlet end of the fluid conduit (35) to achieve accurate and reproducible spraying of the anesthetic onto the larynx.

Preferably, the laryngoscope of the present invention includes a means for illuminating the larynx and pharynx of the patient during the laryngoscopy procedure. In the preferred embodiment shown in FIGS. 1, 2a, and 2b illumination is provided by a light bulb (72) and batteries (73) located in the handle and a fiber optic (74) located in the blade member, the fiber optic having a proximate end in optical communication with the bulb and a distal end located at the distal end of the blade member.

Figure 4:
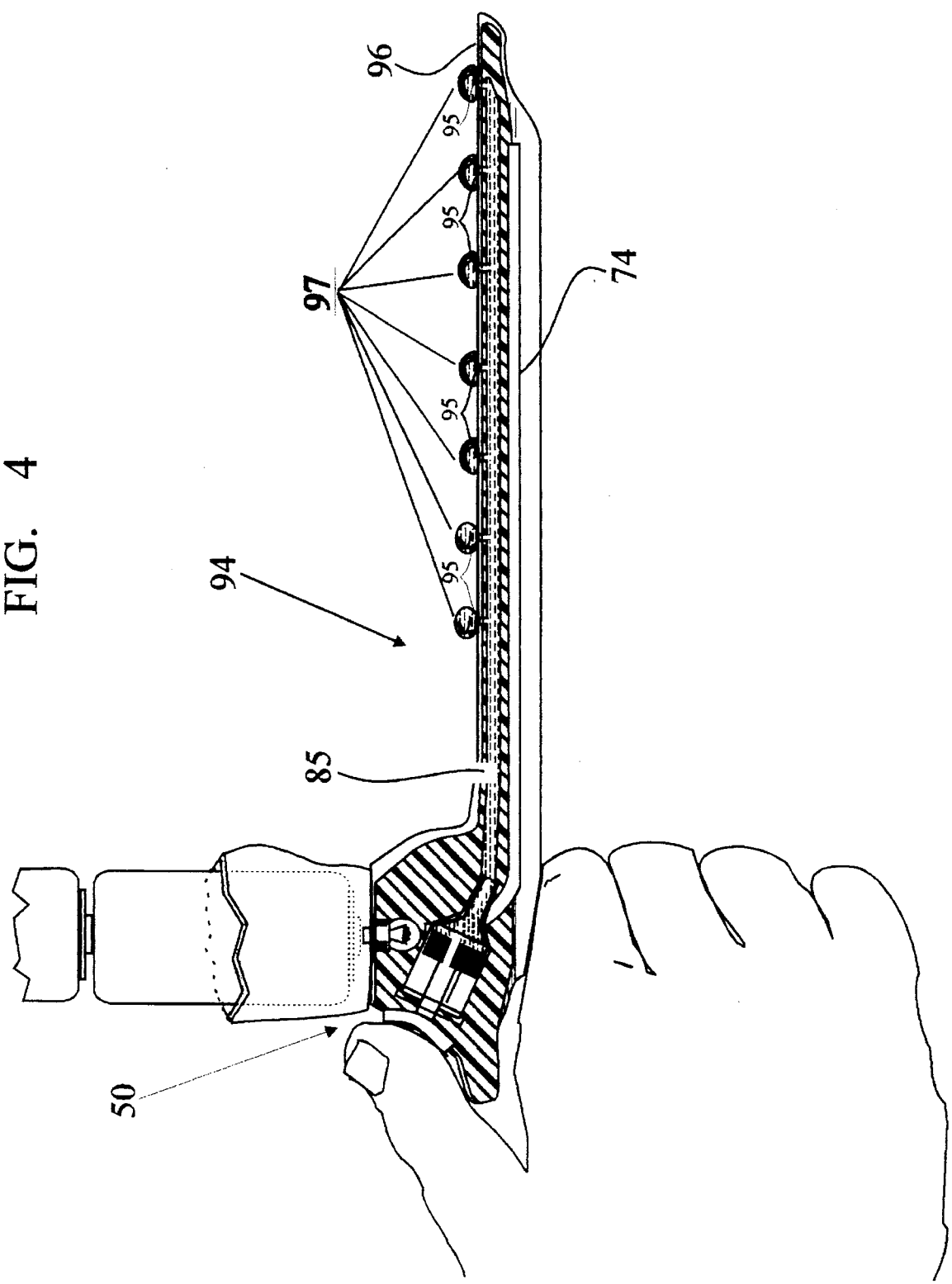
FIG. 4 shows the embodiment of FIG. 3 in operation.

FIGS. 3 and 4 shows a second preferred embodiment of the present invention which provides means for delivering a topical anesthetic gel to the upper surface of the blade member. In this embodiment, the topical anesthetic is preferably in gel form so that the anesthetic remains localized on the surface of the blade, however, the active anesthetic agents are the same as described above.

In this embodiment, the blade (94) includes a fluid conduit manifold (85) for providing fluid communication between a syringe (50) and the upper surface of the blade member (96). The manifold includes outlet holes (95). Thus, when anesthetic gel is expelled from the syringe, it is deposited on the surface of the blade member, thereby coating the surface of the blade member with anesthetic.

FIG. 4 shows the gel-dispensing embodiment in operation. In this embodiment, prior to insertion of the blade member into a patient's mouth, the physician depresses the syringe thereby depositing the anesthetic gel (97) onto the upper surface of the blade member. Once the blade member is coated, it is then inserted into the patients mouth.

FIGS. 5a, 5b, 6a, and 6b show a third preferred embodiment of the present invention which provides an alternative means for delivering a topical anesthetic gel to the upper surface of the blade. In this embodiment, an anesthetic-saturated porous layer (100) is located on the top surface (105) of a blade (110).

The porous layer (100) is made from any material having a porous structure, e.g., sintered glass, polymer membranes, sponge, or any other like material having a porous structure. Preferably, the material forming the porous layer has an elastic compressibility, e.g., natural sponge, rubber, or any other like materials.

Before use, the porous layer is covered by a sheath (115) to prevent evaporation of the anesthetic gel. The sheath is removed from the porous layer immediately prior to insertion of the laryngoscope into the mouth of the patient.

Although only a few embodiments have been described in detail above, those having ordinary skill in the medical arts will clearly understand that many modifications are possible in the preferred embodiment without departing from the teachings thereof. All such modifications are intended to be encompassed within the following claims. For example, the fluid delivery means may be provided by forming the reservoir with a compressible outer wall, allowing the operator to dispense the anesthetic by pressing on the outer wall of the reservoir.

I claim:

1. A laryngoscope blade comprising:
    a blade member having proximate and distal ends, the proximate end of the blade member king adapted for attaching to one end of a handle;
    a reservoir for containing a topical anesthetic, the reservoir being attached directly to the blade member;
    a fluid delivery means in fluid communication with the topical anesthetic for expelling the topical anesthetic from the reservoir; and
    a fluid conduit for providing fluid communication between the reservoir and the distal end of the blade member.

2. The blade of claim 1 wherein the fluid delivery means is a syringe.

3. A laryngoscope blade comprising:
    a blade member having proximate and distal ends, the proximate end of the blade member being adapted for attaching to one end of a handle;
    a reservoir for containing a topical anesthetic gel, the reservoir being attached to the blade member;
    a fluid delivery means in fluid communication with the topical anesthetic gel for expelling the topical anesthetic gel from the reservoir; and
    a fluid conduit manifold for providing fluid communication between the reservoir and an upper surface of the blade member through outlet holes in the upper surface.

4. The blade of claim 3 wherein the fluid delivery means is a syringe.

* * * * *